United States Patent [19]
Pamukcu et al.

[11] Patent Number: 5,990,117
[45] Date of Patent: Nov. 23, 1999

[54] METHOD FOR INHIBITING NEOPLASTIC CELLS AND RELATED CONDITIONS BY EXPOSURE TO QUINAZOLINE DERIVATIVES

[75] Inventors: Rifat Pamukcu, Spring House; Gary Piazza, Doylestown, both of Pa.

[73] Assignee: Cell Pathways, Inc., Horsham, Pa.

[21] Appl. No.: 09/060,443

[22] Filed: Apr. 15, 1998

[51] Int. Cl.[6] .................................................. A01N 43/54
[52] U.S. Cl. .......................................................... 514/259
[58] Field of Search ............................................. 514/259

[56] References Cited

U.S. PATENT DOCUMENTS

| | | | |
|---|---|---|---|
| 3,031,450 | 4/1962 | Fischer et al. | 260/247.5 |
| 3,161,654 | 12/1964 | Shen | 260/319 |
| 3,322,755 | 5/1967 | Roch et al. | 260/246 |
| 3,517,005 | 6/1970 | Cronin et al. | 260/256.4 |
| 3,594,480 | 7/1971 | Cronin et al. | 424/250 |
| 3,647,858 | 3/1972 | Hinkley et al. | 260/470 |
| 3,654,349 | 4/1972 | Shen et al. | 260/515 |
| 3,780,040 | 12/1973 | Schnettler et al. | 260/256.5 |
| 3,812,127 | 5/1974 | Cronin et al. | 260/268 BQ |
| 3,819,631 | 6/1974 | Broughton et al. | 260/256.4 F |
| 3,920,636 | 11/1975 | Takahasi et al. | 260/240 J |
| 4,001,237 | 1/1977 | Partyka et al. | 260/256.4 B |
| 4,001,238 | 1/1977 | Partyka et al. | 260/256.4 B |
| 4,039,544 | 8/1977 | Broughton et al. | 260/256.4 F |
| 4,060,615 | 11/1977 | Matier et al. | 260/256.4 Q |
| 4,079,057 | 3/1978 | Juby et al. | 260/256.4 Q |
| 4,098,788 | 7/1978 | Crenshaw et al. | 544/293 |
| 4,101,548 | 7/1978 | Crenshaw et al. | 544/293 |
| 4,102,885 | 7/1978 | Crenshaw et al. | 544/280 |
| 4,138,561 | 2/1979 | Crenshaw et al. | 544/284 |

(List continued on next page.)

FOREIGN PATENT DOCUMENTS

| | | |
|---|---|---|
| 0 347146 A2 | 12/1989 | European Pat. Off. . |
| 0 349239 A2 | 1/1990 | European Pat. Off. . |
| 0 351058 | 1/1990 | European Pat. Off. . |
| 0 352960 A2 | 1/1990 | European Pat. Off. . |
| 0 395328 A2 | 10/1990 | European Pat. Off. . |

(List continued on next page.)

OTHER PUBLICATIONS

Waddell, W.R. et al., Am. J. Surgery, vol. 157, pp. 175–179 (1989).

Gonzaga, R.A.F. et al., The Lancet, Mar. 30, 1985, p. 751.

Waddell, W.R. et al., J. Surg. Oncology, vol. 24, pp. 83–87 (1983).

Federation Proceedings (1972) of the Federation of American Societies for Experimental Biology abstract Nos. 2044 and 2045.

Gilman, S.C. et al., Nonsteroidal Anti–inflammatory Drugs in Cancer Therapy, (circa 1985).

Brogden, R.N. et al., Drugs, vol. 16, pp. 97–114 (1978).

Hucker, H.B. et al., Drug Metabolism & Disposition, vol. 1, No. 6, pp. 721–736 (1973).

Shen, T.Y. et al., Chemical and Biological Studies on Indomethacin, Sulindac and Their Analogs, pp. 107–178 (circa 1975).

Duggan, D.E. et al., Clin. Pharm. & Therapeutics, vol. 21, No. 3, pp. 326–335 (1976).

Duggan, D.E. et al., J. Pharm. & Exper. Therap., vol. 201, No. 1, pp. 8–13 (1977).

Glavin, G.B. et al., Toxicology and Applied Pharmacology, vol. 83, pp. 386–389 (1986).

Moorghen, M. et al., Journal of Pathology, vol. 156, pp. 341–347 (1988).

Moorghen, M. et al., Acta Histochemica, Suppl.–Band XXIX, S. 195–199 (1990).

Bjarnason et al., Gastroenterology, vol. 94, No. 4, pp. 1070–1074 (1988).

Badrieh, Y., et al., Chem. Ber., vol. 125, pp. 667–674 (1992).

Silvola, J. et al., Effects of nonsteroidal anti–inflammatory drugs on rat gastric mucosal phosphodiesterase activity, Agents and Actions, vol. 12.4, pp. 516–520 (1982).

Curtis–Prior, P.B. et al., Cyclic Nucleotide Phosphodiesterase Activity of Human Normal and Carcinomatous Lung Tissue, The Lancet, pp. 1225–1225 Dec. 4, 1976.

Pepin, P. et al., Effects of Sulindac and Oltipraz on the tumorigenicity of 4–(methylnitrosamino)1–(3–pyridyl)–1–Butanone in A/J mouse lung, Carcinogenesis, vol. 13, No. 3, pp. 341–348 (1992).

Nicholson, C.D. et al. Differential modulation of tissue function and therapeutic potential of selective inhibitors of cyclic nucleotide phosphodiesterase isoenzymes, Trends Pharmacol. Sci. (TiPS), vol. 12, pp. 19–27 (1991).

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Luginer, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Turner, N.C. et al., Relaxation of guinea–pig trachea by cyclic AMP phosphodiesterase inhibitors and their enhancement by sodium mitroprusside, Br. J. Pharmacol. vol. III, pp. 1047–1052 (1994).

Weishaar, R.E. et al., Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

(List continued on next page.)

*Primary Examiner*—Jerome D. Goldberg
*Attorney, Agent, or Firm*—Robert W. Stevenson

[57] ABSTRACT

A method for inhibiting neoplastic cells and related conditions by exposing them to substituted quinazoline compounds.

10 Claims, No Drawings

U.S. PATENT DOCUMENTS

| | | | |
|---|---|---|---|
| 4,146,718 | 3/1979 | Jenks et al. | 544/292 |
| 4,161,595 | 7/1979 | Kaplan et al. | 544/284 |
| 4,171,363 | 10/1979 | Crenshaw et al. | 544/284 |
| 4,208,521 | 6/1980 | Crenshaw et al. | 544/250 |
| 4,209,623 | 6/1980 | Juby | 544/319 |
| 4,423,075 | 12/1983 | Dvornik et al. | 424/317 |
| 4,460,590 | 7/1984 | Möller | 424/251 |
| 4,460,591 | 7/1984 | DeGraw et al. | 424/251 |
| 4,880,810 | 11/1989 | Lowe, III et al. | 514/258 |
| 4,885,301 | 12/1989 | Coates | 514/263 |
| 4,923,874 | 5/1990 | McMahon et al. | 514/258 |
| 5,073,559 | 12/1991 | Coates | 514/262 |
| 5,147,875 | 9/1992 | Coates et al. | 544/259 |
| 5,223,501 | 6/1993 | Chakravarty et al. | 514/258 |
| 5,250,535 | 10/1993 | Verheyden et al. | 514/262 |
| 5,254,571 | 10/1993 | Coates et al. | 514/340 |
| 5,358,952 | 10/1994 | Moschel et al. | 514/262 |
| 5,401,774 | 3/1995 | Pamukcu et al. | 514/569 |
| 5,439,895 | 8/1995 | Lee et al. | 514/63 |
| 5,488,055 | 1/1996 | Kumar et al. | 514/293 |
| 5,614,530 | 3/1997 | Kumar et al. | 544/293 |
| 5,614,627 | 3/1997 | Takase et al. | 544/293 |

FOREIGN PATENT DOCUMENTS

| | | |
|---|---|---|
| 0 428268 A2 | 5/1991 | European Pat. Off. . |
| 0 463756 A1 | 1/1992 | European Pat. Off. . |
| 0 485157 A2 | 5/1992 | European Pat. Off. . |
| 0 485158 A2 | 5/1992 | European Pat. Off. . |
| 0 485171 A2 | 5/1992 | European Pat. Off. . |
| 0 485172 A2 | 5/1992 | European Pat. Off. . |
| 0 485173 A2 | 5/1992 | European Pat. Off. . |
| 0 508586 A1 | 10/1992 | European Pat. Off. . |
| 0 526004 A1 | 2/1993 | European Pat. Off. . |
| 0 607439 A1 | 7/1994 | European Pat. Off. . |
| 3038166 | of 1981 | Germany . |
| 56-53659 | 5/1981 | Japan . |
| 57-167974 | 10/1982 | Japan . |
| 807826 | 1/1959 | United Kingdom . |
| 2063249 | 6/1981 | United Kingdom . |
| WO 92/03419 | 3/1992 | WIPO . |
| WO 93/07149 | 4/1993 | WIPO . |
| WO 93/12095 | 6/1993 | WIPO . |
| WO 94/05661 | 3/1994 | WIPO . |
| WO 97/03985 | 2/1997 | WIPO . |

OTHER PUBLICATIONS

Saeki, T. et al., Isolation of Cyclic Nucleotide Phosphodiesterase Isozymes From Pig Aorta, Biochem. Pharmacology, vol. 46, No. 5, pp. 833–839 (1993).

Turner, N.C. et al., Pulmonary effects of type V cyclic GMP specific phosphodiesterase inhibition in anaesthetized guinea–pig, Br. J. Pharmacol., vol. 111, 1198–1204 (1994).

Ferreira, S.H. et al., The molecular mechanism of action of peripheral morphone analgesia: stimulation of the cGMP system via nitric oxide release, European Journal of Pharmacology, 201 pp. 121–122 (1991).

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Tulshian, D. et al., Synthesis and Phosphodiesterase Activity of Carboxylic Acid Mimetics of Cyclic Guanosine 3",5"–Monophosphate, J. Med. Chem, vol. 36, 1210–1220 (1993).

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073,2081 (1992).

Broughton, B.J. et al., Antiallergic Activity of 2–Phenyl–8–azapruin–6–ones, Journal of Medicinal Chemistry, vol. 18, No. 11, pp. 1117–1118 (1975).

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Zacharski, L. R. et al., Effect of Mopidamol on Survival in Carcinoma of the Lung and Colon: Final Report of Veterans Administration Cooperative Study No. 188, J. of the Nat'l. Cancer Inst., vol. 80, No. 2, pp. 90–96 (1988).

Lichtner, R. B. et al., The Pyrimido–pyrimidine Derivatives RA 233 and RX–RA 85 affect Growth adn Cytoskeletal Organization of Rat Mammary Adenocarcinoma Cells, Eur. J. Cancer Clin. Oncol., vol. 23, No. 9, pp. 1269–1275 (1987).

Janik, P. et al., Inhibition of Growth of Primary and Metastatic Lewis Lung Carcinoma Cells by the Phosphodiesterase Inhibitor Isobutylmethylxanthine, Cancer Res. vol. 40, pp. 1950–1954, (Jun., 1980).

Bergstrand, Hakan et al., Effects of Antiallergic Agents, Compound 48/80, and Some Reference Inhibitors on the Activity of Partially Purified Human Lung Tissue Adenosine Cyclic 3',5'–Monophosphate and Guanosine Cyclic 3',5'–Monophosphate Phosphodiesterases, Molecular Pharmacology, 13, pp. 38–43 (1976).

Drees, Markus et al., 3',5'–Cyclic Nucleotide Phosphodiesterase in Tumor Cells as Potential Target for Tumor Growth Inhibition, Cancer Research 53, pp. 3058–3061 (1993).

Semmler, J. et al., Xanthine derivatives: comparison between suppression of tumor necrosis factor–x production and inhibition of cAMP phosphodiesterase activity, Immunology 78, pp. 520–525 (1993).

Mehta, Rajendra et al., Structure–Activity Relationships of Brassinin in Preventing the Development of Carcinogen–Induced Mammary Lesions in Organ Culture, Anticancer Research 14: 1209–1214 (1994).

Makaryan, A.P. et al., Cyclic Nucleotides in Patients with Malignant Neoplasms of the Colon, Laboratornoe Delo, vol. 8, pp. 31–33 (1991).

Carter et al., Chemotherapy of Cancer, $2^{nd}$ Ed., John Wiley & Sons, NY, NY, 1981, pp. 362–365.

Biddle, William et al., Antineoplastic Effect of the Pyrimido–Pyrimidine Derivative: RA 233, Pathologie Biologie, Jan., 1984, pp. 9–13.

Clarke, W.R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2), pp. 81–89, (1994).

Raeburn, David et al., Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–1151 (1993).

Marcoz, P. et al., Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–1035 (1993).

Barnett, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–812 (1993).

Molnar–Kimber, K. et al., Modulation of TNFa and IL–1B from indotoxin–stimulated monocytes by selective PDE isozyme inhibitors (Abstract Only), Agents Actions 39(Spec. Conf. Issue), C77–C79 (1993).

Giorgi, Mauro et al., Characterization of 3':5' cyclic nucleotide phosphodiesterase activities of mouse neuroblastoma N18TG2 cells (Abstract Only), FEBS Lett. 324(1) pp. 76–80 (1993).

Porter, Roderick et al., Preparation of 6–phenyl–3–(5–tetrazoly)pyridin–2(H)–one derivatives as cyclic AMP–dependent protein kinase agonists (Abstract Only), PCT Int. Appl. WO9206085 A1, (Sep. 26, 1991).

Molnar–Kimber, K. L. et al., Differential regulation of TNF–a and IL–1B production from endotoxin stimulated human monocytes by phosphodiesterase inhibitors (Abstract Only), Mediators Inflammation 1(6) pp. 411–417 (1992).

Radomski, Marek W. et al., Human Colorectal adenocarcinoma cells: differential nitric oxide synthesis determines their ability of aggregate platelets (Abstract Only), Cancer Res. 51(22) pp. 6073–6078 (1991).

Anderson, Thomas L. G. et al., Interactions between isoprenaline, sodium nitroprusside, and isozyme–selective phosphodiesterase inhibitors on ADP–induced aggretation and cyclic Nucleotide levels in human platelets (Abstract Only), J. Cardiovasc. Pharmacol. 18(2) pp. 237–242 (1991).

Souness, John E. et al., Role of Selective cyclic GMP phosphodiesterase inhibition in the myorelaxant actions of M&B 22,943, MY–5445, vinpocetine and 1–methyl–3–isobutyl–8–(methylamino)xanthine (Abstract Only), Br. J. Pharmacol. 98(3) pp. 725–734 (1989).

Lichtner, Rosemarie B., The pyrimidopyrimidine derivatives RA233 and RX–RA85 affect cell cycle distribution of two murine tumor cell lines (Abstract Only), Eur. J. Cancer Clin. Oncol. 25(6), pp. 945–951 (1989).

Mamytbekova, A., et al., Antimetastatic effect of flurbiprofen and other platelet aggregation inhibitors (Abstract Only), Neoplasma 33(4), pp. 417–421 (1986).

Hagiwara, Masatoshi et al., Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–471 (1984).

METHOD FOR INHIBITING NEOPLASTIC CELLS AND RELATED CONDITIONS BY EXPOSURE TO QUINAZOLINE DERIVATIVES

TECHNICAL FIELD

This invention relates to a method for the selective inhibition of neoplastic cells, for example, for the treatment or prevention of precancerous lesions or other neoplasias in mammals.

BACKGROUND OF THE INVENTION

Each year in the United States alone, untold numbers of people develop precancerous lesions, which is a form of neoplasia, as discussed below. Such lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds that prevent or induce the remission of existing precancerous or cancerous lesions or carcinomas would greatly reduce illness and death from cancer.

For example, approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation which can be fatal. Overall, about $2.5 billion is spent annually in the United States in colon cancer treatment and prevention.

In the breast, breast cancer is often treated surgically, often by radical mastectomy with its painful and emotional aftermath. Such surgery is costly, too.

As indicated above, each lesion carries with it a chance that it will develop into a cancer. The likelihood of cancer is diminished if a precancerous lesion is removed. However, many of these patients demonstrate a propensity for developing additional lesions in the future. They must, therefore, be monitored periodically for the rest of their lives for reoccurrence.

In most cases (i.e. the cases of sporadic lesion formation, e.g. so-called common sporadic polyps), lesion removal will be effective to reduce the risk of cancer. In a small percentage of cases (i.e. cases where numerous lesions form, e.g. the so-called polyposis syndromes), removal of all or part of the effected area (e.g. the colon) is indicated. For example, the difference between common sporadic polyps and polyposis syndromes is dramatic. Common sporadic polyp cases are characterized by relatively few polyps that can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each lesion carries with it a palpable risk of cancerous development, patients who form many lesions (e.g. polyposis syndrome patients) invariably develop cancer if left untreated. Surgical removal of the colon is the conventional treatment in polyposis patients. Many polyposis patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because chemotherapy for cancer itself is often not effective and has severe side effects. Cancer chemoprevention is important for recovered cancer patients who retain a risk of cancer reoccurrence. Also, cancer prevention is important for people who have not yet had cancer, but have hereditary factors that place them at risk of developing cancer. With the development of new genetic screening technologies, it is easier to identify those patients with high-risk genetic factors, such as the potential for polyposis syndrome, who would greatly benefit from chemopreventative drugs. Therefore, finding such anti-cancer drugs that can be used for prolonged preventive use is of vital interest.

Known chemopreventative and chemotherapeutic drugs are believed to kill cancer cells by inducing apoptosis, or as sometimes referred to as "programmed cell death." Apoptosis naturally occurs in virtually all tissues of the body, and especially in self-renewing tissues such as bone marrow, gut, liver and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis play a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long-term use, or use in otherwise healthy individuals with precancerous lesions. These side effects, which are a result of nonspecific cytotoxicity of the drugs, include hair loss, weight loss, vomiting, immune suppression and other toxicities. For this reason, there is a need to identify new drug candidates for therapy of patients with precancerous lesions that do not have such serious side effects in humans.

In recent years, several nonsteroidal anti-inflammatory drugs ("NSAIDs"), originally developed to treat arthritis, have shown effectiveness in inhibiting and eliminating colonic polyps. Polyps virtually disappear when the patients take such drugs, particularly when the NSAID sulindac is administered. However, the prophylactic use of currently available NSAIDs, even in polyposis syndrome patients, is marked by severe side reactions that include gastrointestinal irritations and ulcerations. Once NSAID treatment is terminated due to such complications, the polyps return, particularly in polyposis syndrome patients.

Sulindac has been particularly well received among the NSAIDs for the polyp treatment. Sulindac is a sulfoxide compound that itself is believed to be inactive as an antiarthritic agent. The sulfoxide is reportedly converted by liver enzymes to the corresponding sulfide, which is acknowledged to be the active moiety as a prostaglandin synthesis inhibitor. The sulfide, however, is associated with the side effects of conventional NSAIDs. The sulfoxide is also known to be metabolized to sulfone compound that has been found to be inactive as an inhibitor of prostaglandin synthesis but active as an inhibitor of precancerous lesions.

SUMMARY OF THE INVENTION

This invention includes a method of inhibiting neoplastic cells by exposing those cells to a pharmacologically effective amount of those compounds described below. Such compounds are effective in modulating apoptosis and eliminating and inhibiting the growth of neoplasias such as precancerous lesions.

The compounds of that are useful in the methods of this invention include those of Formula I:

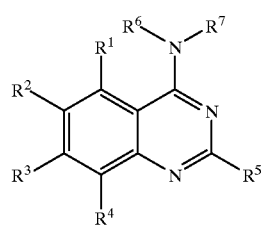

(I)

wherein $R_1$, $R_2$, $R_3$, $R_4$ and $R_5$ are independently selected from the group consisting of hydrogen, halogen, lower alkyl, or lower alkoxy; and $R_6$ and $R_7$ are independently selected from the group consisting of hydrogen, lower alkyl, hydroxyalkyl, lower alkoxyalkyl, cyanoalkyl, heteroarylalkyl, cycloalkyl, cycloalkylalkyl or carboxyl alkyl which may be protected, or alternatively $R_6$ and $R_7$ form a ring together with the nitrogen atom to which they are bonded, said ring selected from the group consisting of piperadino, pyrrolidino, morpholino and piperazino that can optionally be substituted with one or two substituents selected from the group consisting of lower alkyl, carboxyl (which may be protected), cyano, acyl, amino, alkylamino, dialkylamino, aminoalkyl, alkylaminoalkyl, carbamoyl, halobenzoyl, halo-α-hydroxybenzoyl, alkylamino, dialkylamino, piperadino, oxo, hydroxy, pyridyl, and pyrimidyl.

DETAILED DESCRIPTION OF THE INVENTION

The present invention also is a method of treating a patient with such lesions by administering to a patient a pharmacologically effective amount of a pharmaceutical composition that includes a compound of Formula I, wherein $R_1$ etc. are as defined above. Preferably, this composition is administered without therapeutic amounts of an NSAID.

The present invention is also a method of treating individuals with neoplastic lesions by administering a pharmacologically effective amount of an enterically coated pharmaceutical composition that includes compounds of this invention.

Also, the present invention is a method of inhibiting the growth of neoplastic cells by exposing the cells to an effective amount of compounds of Formula I, wherein $R_1$ through $R_7$ and Y are defined as above.

In still another form, the invention is a method of inducing apoptosis in human cells by exposing those cells to an effective amount of compounds of Formula I, wherein $R_1$ etc. are defined as above where such cells are sensitive to these compounds.

Additionally, in yet another form, the invention is a method of treating a patient having a disease which would benefit from regulation of apoptosis by treating the patient with an effective amount of compounds of Formula I, wherein $R_1$ etc. are defined as above. The regulation of apoptosis is believed to play an important role in diseases associated with abnormalities of cellular growth patterns such as benign prostatic hyperplasia, neurodegenerative diseases such as Parkinson's disease, autoimmune diseases including multiple sclerosis and rheumatoid arthritis, infectious diseases such as AIDS, and other diseases, as well.

As used herein, the term "precancerous lesion" includes syndromes represented by abnormal neoplastic, including dysplastic, changes of tissue. Examples include dysplasic growths in colonic, breast, bladder or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, prostatic dysplasia, bronchial dysplasia, breast, bladder and/or skin and related conditions (e.g., actinic keratosis), whether the lesions are clinically identifiable or not.

As used herein, the term "carcinomas" refers to lesions that are cancerous. Examples include malignant melanomas, breast cancer, prostate cancer and colon cancer.

As used herein, the term "neoplasm" refers to both precancerous and cancerous lesions and hyperplasia.

As used herein, the term "lower alkyl" means a linear or branched alkyl group having 1 to 6 carbon atoms, for example, methyl, ethyl, n-propyl, n-butyl, isopropyl, isobutyl, 1-methylpropyl, tert-butyl, n-pentyl, 1-ethylpropyl, isoamyl and n-hexyl. The most preferred include methyl group and ethyl group.

The term "lower alkoxy" includes but are not limited to methoxy, ethoxy, propoxy, butoxy and the like which are derived from the above lower alkyl groups. The preferable include methoxy and ethoxy, and the most preferrable is methoxy.

The term "hydroxyalkyl" refers to where one or, two or more hydroxyl group(s) is(are) bonded to any of the carbon atoms in a lower alkyl group.

The term "lower alkoxyalkyl" refers the case wherein one or, two or more lower alkoxy group(s) defined above is (are) bonded to any of the carbon atoms an alkyl group.

The term "cyanoalkyl" refers to the case wherein one or two or more cyano group(s) is (are) bonded to any of the carbon atoms of a lower alkyl group.

The term "heteroarylalkyl" refers to the case wherein one or two or more heteroaryl group(s) is (are) bonded to any of the carbon atoms of a lower alkyl group. The term "heteroaryl" means a five- to six-membered ring containing one to three nitrogen atom, sulfur atom and/or oxygen atom, and preferable ones include aromatic rings containing one or two nitrogen atoms, such as imidazolyl group, pyridyl group and pyrimidyl group.

The term "cycloalkyl" refers to an alkyl ring having 3 to 8 carbon atoms, and preferably ones include those having 5 to 6 carbon atoms.

The term "cycloalkylalkyl" refers to a cycloalkyl group that is bonded to any of the carbon atoms of a lower alkyl group.

The alkyl group in the "carboxyl alkyl" group, which may be protected, is a lower alkyl. The carboxyl group may be bonded to any of the carbon atoms of that lower alkyl group. Protective groups for the carboxyl include lower alkyl; phenyl-substituted lower alkyl groups wherein the phenyl group may have a substituent, such as p-methoxybenzyl, p-nitrobenzyl, 3,4-dimethoxybenzyl, diphenylmethyl, tributyl and phenethyl; halogenated lower alkyl groups such as 2,2,2-trichloroethyl and 2-iodoethyl; lower alkanoyloxy lower alkyl groups such as pivaloyloxymethyl, acetoxymethyl, propionyloxymethyl, butyryloxymethyl, valeryloxymethyl, 1-acetoxyethyl, 2-acetoxyethyl, 1-pivaloyloxyethyl and 2-pivaloyloxyethyl; higher alkanoyloxy lower alkyl groups such as palmitoyloxyethyl, heptadecanoyloxymethyl and 1-palmitoyloxyethyl; lower alkoxycarbonyloxy lower alkyl groups such as methoxycarbonyloxymethyl, 1-butoxycarbonyloxyethyl and 1-(isopropoxycarbonyloxy)ethyl; carboxy lower alkyl groups such as carboxymethyl and 2-carboxyethyl; a heterocyclic group such as 3-phthalidyl; benzoyloxy lower alkyl groups which may have a substituent, such as 4-glycyloxybenzoyloxymethyl and 4-[N-(t-butoxycarbonyl)glycyloxy]benzoyloxymethyl; a (substituted dioxolene) lower alkyl group such as (5-methyl-2-oxol,3-dioxolen-4-yl)methyl; a cycloalkyl-substituted lower alkanoyloxy lower alkyl group such as 1-cyclohexylacetyloxyethyl; and a cycloalkyloxycarbonyloxy lower alkyl group such as 1-cyclohexyloxycarbonyloxyethyl.

Further, protective groups include the various acid amides that can release a carboxyl group by the decomposition thereof in vivo. The quinazoline compounds useful in the present invention can exhibit drug efficacy either by decomposing the protective group in vivo or as such.

The term "halogen" or "halo" means fluorine, chlorine, bromine and iodine.

The pharmacologically acceptable salt according to the present invention includes inorganic acid salts such as hydrochloride, sulfate, hydrobromide and phosphate; and organic acid salts such as formate, acetate, trifluoroacetate, maleate, fumarate, tartrate, methanesulfonate, benzenesulfonate and toluenesulfonate.

Some of the compounds above may form hydrates, which also fall within the scope of the present invention.

Desirable examples of compounds useful in the practice of this invention include quinazoline compounds of Formula I and pharmacologically acceptable salts thereof wherein $R_1$–$R_5$ are independently selected from the group consisting of hydrogen, halogen, lower alkyl or lower alkoxy; and $R_6$ and $R_7$ are independently selected from the group consisting of hydrogen, lower alkyl or a carboxyl alkyl (which may be protected), or alternatively $R_6$ and $R_7$ may form a substituted or unsubstituted ring together with the nitrogen atom to which they are bonded, this ring selected from the group consisting of piperidino and pyrrolidino.

Among the desirable compounds above, still more desirable compounds useful in this invention include quinazoline compounds of Formula I or pharmacologically acceptable salts thereof wherein $R_1$ and $R_5$ are hydrogen, and $R_2$, $R_3$ and $R_4$ are independently selected from the group consisting of halogen or lower alkoxy.

Further, the most desirable compounds among those desirable compounds are those wherein $R_1$ and $R_5$ are hydrogen, and $R_2$, $R_3$ and $R_4$ are lower alkoxy, preferably methoxy and wherein $R_6$ and $R_7$ are independently selected from the group consisting of hydrogen, n-propyl or carboxypropyl (which may be protected), or alternatively $R_6$ and $R_7$ may form a substituted or unsubstituted piperidine ring together with the nitrogen atom to which they are bonded.

Where $R_6$ and $R_7$ form a piperidine ring is preferable, and compounds wherein this piperidine ring has a carboxyl group which may be protected at the 4-position thereof are the most preferable.

The main processes for preparing compounds useful in this invention are described in U.S. Pat. No. 5,614,627 and are set forth below. Compounds represented by the general Formula I can be prepared by the following process:

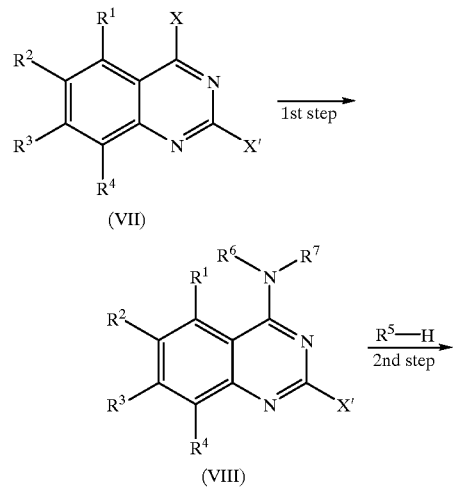

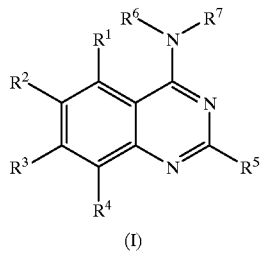

wherein $R_1$, $R_2$, $R_3$, $R_4$, $R_5$, $R_6$ and $R_7$ each has the meaning described above; and X and X' may be the same or different from each other and each means a halogen atom.

The first step is a conventional condensation reaction. Although it is preferable to use an alcoholic solvent such as isopropyl alcohol, an etheric solvent such as tetrahydrofuran, or dimethylformamide as the reaction solvent, any organic solvent inert to the reaction can be used. When the reaction is made to proceed in the presence of a tertiary amine such as triethylamine under reflux by heating with the removal of formed hydrochloric acid, still preferable results are reportedly attained.

The second step is a reaction which comprises condensing compound VIII obtained in the first step with a compound represented by the general formula $R_5$—H by a conventional process. Although it is preferable to use an alcoholic solvent such as isopropyl alcohol, an etheric solvent such as tetrahydrofuran, or dimethylformamide as the reaction solvent, any organic solvent inert to the reaction can be used. In the second step, it is preferable that the reaction is conducted under reflux by heating in the presence of an organic base such as triethylamine, pyridine and ethyldiisopropylamine; an inorganic base such as sodium carbonate, potassium carbonate, sodium hydrogencarbonate, sodium hydride and sodium hydroxide; an alkoxide such as sodium methoxide and potassium t-butoxide; or the like.

Another process for making certain compounds useful in this invention wherein $R_1$, $R_3$ or $R_4$ in Formula I is a hydrogen atom is the following:

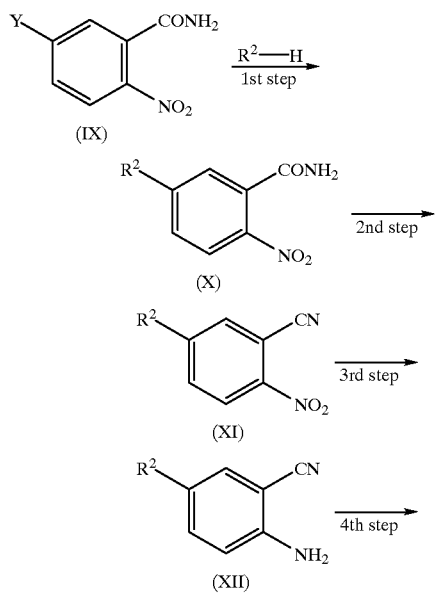

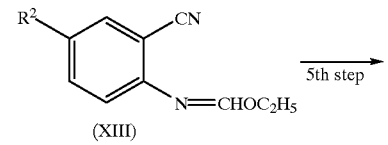

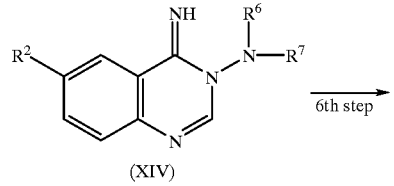

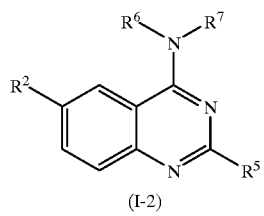

the base include potassium carbonate, hydrides of alkali metals and alkaline earth metals such as lithium hydride and calcium hydride; alkoxides such as potassium t-butoxide and sodium ethoxide; sodium amide and the like.

The second step is a reaction that yields a compound XI by dehydrating the benzamide derivative obtained in the first step. Although the reaction is generally conducted under heating, the reaction reportedly proceeds sufficiently even at room temperature. Preferable examples of the dehydrating reagent include trifluoroacetic anhydride, thionyl chloride, chlorosulfonyl isocyanate, p-toluenesulfonyl chloride, phosphorus pentachloride, phosphorus oxychloride and the like. Preferable examples of the reaction solvent include etheric solvents such as tetrahydrofuran and dioxane, acetonitrile, N,N-dimethylformamide, triethylamine, pyridine and the like, though any one, which is inert to the reaction, can be used.

The third step is a reaction yielding an aniline derivative represented by Formula XII by reducing the nitrobenzene derivative obtained in the second step. It is preferable that the reaction is conducted in a polar solvent, for example, water or an alcoholic solvent such as methanol and ethanol. The reaction is generally made to proceed under acidic conditions with acetic acid or hydrochloric acid by the addition of a metal such as iron, tin or zinc. The reaction temperature ranges from room temperature to the refluxing temperature of the solvent.

The fourth step is a reaction that yields a compound of Formula XIII by heating in ethyl orthoformate in the presence of an acid such as trifluoroacetic acid, p-toluenesulfonic acid and concentrated hydrochloric acid.

The fifth step involves condensing compound XIII obtained in the fourth step with an amine corresponding to the desired compound through ring closure by a conventional process. As the reaction solvent, alcoholic ones such as methanol and ethanol can be used. The reaction temperature is preferably around 50° C., though it may range from room temperature to the boiling point of the solvent.

The sixth step is a reaction that obtains compound I-2 by heating the compound XIV obtained in the fifth step in a solvent. The preferable reaction solvents include alcoholic solvents such as methanol and ethanol, though any solvent inert to the reaction can be used. Further, more desirable results are reportedly obtained when the reaction is conducted in the presence of an alkali such as aqueous sodium hydroxide and potassium carbonate.

The compounds obtained by the above processes can be converted into salts by a conventional process such as the addition of sodium hydroxide, potassium hydroxide, methanesulfonyl chloride or the like.

Among the starting compounds VII to prepare compounds of Formula (I), the compound (VII') wherein $R_1$, $R_3$ and $R_4$ are hydrogen atoms reportedly can be prepared by the following process:

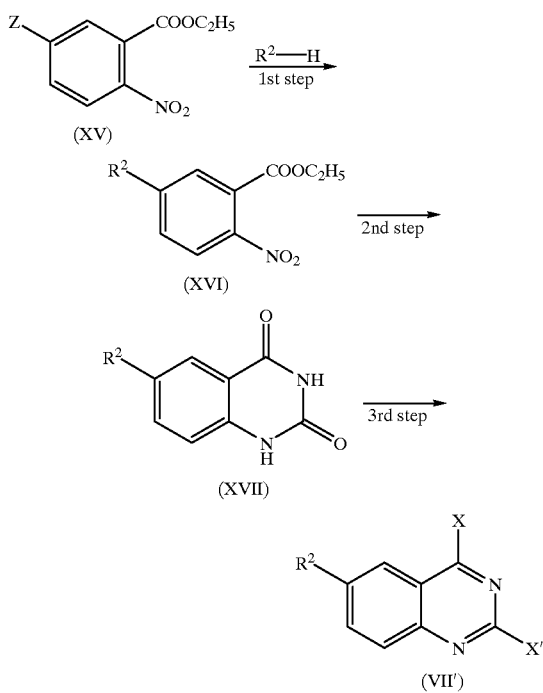

wherein $R_2$, X and X' each has the meaning described above; and Z means a halogen atom.

The first step is a reaction which comprises obtaining a compound (XVI) by treating a benzene derivative with a compound corresponding to the desired compound in a solvent in the presence of a base at a temperature ranging from room temperature to the boiling point of the solvent. Tetrahydrofuran, N,N-dimethylformamide, N-methylpyrrolidone and the like are reportedly preferably used as the solvent, though any solvent inert to the reaction can be used. Preferable examples of the base include potassium carbonate; hydrides of alkali metals and alkaline earth metals such as lithium hydride and calcium hydride; alkoxides such as potassium t-butoxide and sodium ethoxide; sodium amide and the like.

The second step comprises obtaining a compound (XVII) from the compound (XVI) through ring closure by a conventional process, for example, a process which comprises reacting a urea derivative with the compound (XVI) to effect ring closure, and the like may be cited. The reaction temperature in this case is preferably about 170° to 190° C., and preferable examples of the reaction solvent include N-methylpyrrolidone and the like, though any organic solvent inert to the reaction can be used.

The third step is a halogenation reaction that reportedly can be conducted by a conventional process, or, for example, a process which comprises refluxing in the presence of phosphorus pentachloride and phosphorus oxychloride or in the presence of phosphorus oxychloride by heating under stirring to effect chlorination, and the like can be cited.

Compounds useful in the practice of this invention may be formulated into pharmaceutical compositions together with pharmaceutically acceptable carriers for oral administration in solid or liquid form, or for rectal or topical administration, although carriers for oral and parenteral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for rectal administration are preferably suppositories that may contain, in addition to the compounds of this invention excipients such as cocoa butter or a suppository wax, or gel.

When the present invention is used as a medicine for such diseases, it is administered by oral administration or parenteral administration. The dose thereof varies depending upon the extent of symptom; the age, sex, weight and drug sensitivity of a patient; the method, timing and interval of administration; the type of pharmaceutical preparation; the type of a medicine to be administered together therewith; the type of an active ingredient and so forth.

In the oral or by injectible administration, the total daily dose is generally about 0.2 to 150 mg. administered in 1 to 3 doses a day.

The foregoing may be better understood from the following examples from the aforesaid U.S. patent that are presented for purposes illustrating compounds useful in practicing this invention and are not intended to limit the scope of the invention.

EXAMPLE 1

4-(3-Ethoxycarbonylpropyl)Amino-6,7,8-Trimethoxyquinazoline 1.0 g of ethyl 4-aminobutyrate hydrochloride (6.0 mmol), 2 ml of triethylamine, 10 ml of tetrahydrofuran and 10 ml of 2-propanol are added to 0.50 g (2.0 mmol) of 4-chloro-6,7,8-trimethoxyquinazoline, followed by heating under reflux one whole day and night. The reaction liquid is distilled under reduced pressure to remove the solvent. The obtained residue is purified by silica gel column chromatography (ethyl acetate) and then recrystallized from ethyl acetate/hexane. Thus, 0.49 g (yield 72%) of a white crystal is obtained.

Mol. form. $C_{17}H_{23}N_3O_5$

Yield 72%

M.p. 123° to 124° C.

Mass 350 (M++1)

NMR delta (CDCl$_3$); 1.25(3H, t, J=7.2 Hz) 2.10(2H, quintet, J=6.4 Hz) 2.57(2H, t, J=6.4 Hz) 3.68(2H, m) 4.00 (3H, s) 4.03(3H, s) 4.11(3H, s) 4.14(2H, q, J=7.2 Hz) 6.56(1H, br-s) 6.86(1H, s) 8.60(1H, s)

EXAMPLE 2

4-(3-Carboxypropyl)Amino-6,7,8-Trimethoxyquinazoline 5 ml of a 1N aqueous solution of sodium hydroxide is added to a solution of 0.52 g (1.5 mmol) of the 4-(3-ethoxycarbonylpropyl)amino-6,7,8-trimethoxyquinazoline obtained in Example 1 in tetrahydrofuran (5 ml)/ethanol (5 ml), followed by stirring at room temperature one whole day and night. The reaction liquid is neutralized with 5 ml of 1N hydrochloric acid, and then concentrated under reduced pressure. The crystals thus precipitated are recovered by filtration, washed with water, and dried with air. Thus, 0.36 g (yield 744%) of a pale-yellow crystal is obtained.

Mol. form. $C_{15}H_{19}N_3O_5$

Yield 74%

M.p. 236° to 237° C. (dec.)

NMR delta (DMSO-d$_6$); 1.88(2H, quintet, J=7.2 Hz) 2.33(2H, t, J=7.2 Hz) 3.55(2H, m) 3.87(3H, s) 3.91(3H, s) 3.97(3H, s) 7.44(1H, s) 8.04(1H, brt, J=5.4 Hz) 8.35(1H, s)

The following compounds reportedly can be obtained in accordance with the processes of Examples 1 and 2.

EXAMPLE 3

4-(5-Ethoxycarbonylpentyl)Amino-6,7,8-Trimethoxyquinazoline

Mol. form. $C_{19}H_{27}N_3O_5$

Yield 84%

M.p. 128° to 129° C.

Mass 378(M<+>+1)

NMR delta (CDCl$_3$); 1.25(3H, t, J=7.2 Hz) 1.49(2H, m) 1.67–1.80(4H, m) 2.35(2H, t, J=7.0 Hz) 3.68(2H, dt, J=6.8, 6.0 Hz) 3.99(3H, s) 4.03(3H, s) 4.11(3H, s) 4.12(2H, q, J=7.2 Hz) 5.72(1, brs) 6.80(1H, s) 8.61(1H, s)

EXAMPLE 4

4-(5-Ethoxycarbonylpentyl)Amino-6-Chloroquinazoline

Mol. form. $C_{17}H_{20}ClN_3O_2$

Yield 84%

M.p. 117° to 118° C.

Mass 322(M<+>+1)

NMR delta (CDCl$_3$); 1.27(3H, t, J=7.2 Hz) 1.49(2H, m) 1.68–1.80(4H, m) 2.37(2H, t, J=7.0 Hz) 3.71(2H, dt, J=6.8, 5.6 Hz) 4.18(2H, q, J=7.2 Hz) 6.03(1H, br-s) 7.66(1H, dd, J=9.2, 2.4 Hz) 7.77(1H, d, J=9.2 Hz) 7.82(1, d, J=2.4 Hz) 8.64(1H, s)

EXAMPLE 5

4-(Ethoxycarbonylmethyl)Amino-6,7,8-Trimethoxyquinazoline

Mol. form. $C_{15}H_{19}N_3O_5$

Yield 84%

M.p. 182° to 183° C. (dec.)

Mass 322(M<+>+1)

NMR delta (CDCl$_3$); 1.35(3H, t, J=7.2 Hz) 3.94(3H, s) 4.04(3H, m) 4.11(3H, s) 4.31(2H, q, J=7.2 Hz) 4.40(2H,d, J=4.8 Hz) 6.23(1H, brt. J=4.8 Hz) 6.76(1H, s) 8.61(1H, s)

EXAMPLE 6

4-(6-Ethoxycarbonylhexyl)Amino-6,7,8-Trimethoxyquinazoline

Mol. form. $C_{20}H_{29}N_3O_5$

Yield 98%

M.p. 132° to 133° C.

Mass 392(M<+>+1)

NMR delta (CDCl$_3$); 1.25(3H, t, J=7.2 Hz) 1.36–1.51(4H, m) 1.60–1.79(4H, m) 2.31(2H, t, J=7.2 Hz) 3.65(2H, dt, J=7.2,5.6 Hz) 3.98(3H, s) 4.03(3H, s) 4.12(3H, s) 4.13(2H, q, J=7.2 Hz) 5.54(1H, brs) 6.72(1H, s) 8.62(1H, s)

EXAMPLE 7

4-(2-Ethyloxycarbonylethyl)Amino-6,7,8-Trimethoxyquinazoline

Mol. form. $C_{16}H_{21}N_3O_5$

Yield 57%

M.p. 141° to 142° C.

Mass 336 (M<+>+1)

NMR delta (CDCl$_3$); 1.28(3H, t, J=7.2 Hz) 2.76(2H, t, J=6.0 Hz) 3.95(2H, q, J=6.0 Hz) 3.98(3H, s) 4.03(3H, s) 4.12(3H, s) 4.18(2H, q, J=7.2 Hz) 6.23(1H, brs) 6.69(1H, s) 8.61(1H, s)

EXAMPLE 8

4-(4-Ethoxycarbonylbutyl)Amino-6,7,8-Trimethoxyquinazoline

Mol. form. $C_{18}H_{25}N_3O_5$

Yield 35%

M.p. 139° to 140° C.

Mass 364 (M<+>+1)

NMR delta (CDCl$_3$); 1.28(3H, t, J=7.2 Hz) 1.74–1.86(4H, m) 2.44(2H, t, J=6.6 Hz) 3.64(2H, m) 4.00(3H, s) 4.03(3H, s) 4.12(3H, s) 4.16(2H, q, J 7.2 Hz) 6.10(1H, brs) 6.92(1H, s) 8.61(1H, s)

EXAMPLE 9

4-(7-Ethoxycarbonylheptyl)Amino-6,7,8-Trimethoxyquinazoline

Mol. form. $C_{21}H_{31}N_3O_5$

Yield 61%

M.p. 124° to 125° C.

Mass 406(M<+>+1)

NMR delta (CDCl$_3$); 1.25(3H, t, J=7.0 Hz) 1.30–1.48(6H, m) 1.63(2H, m) 1.73(2H, m) 2.30(2H, t, J 7.4 Hz) 3.64(2H, dt, J=7.2, 5.6 Hz) 3.98(3H, s) 4.03(3H, s) 4.12(3H, s) 4.12(2H, q, J=7.0 Hz) 5.53(1H, brs) 6.72(1H, s) 8.62(1H, s)

EXAMPLE 10

4-(5-Carboxypentyl)Amino-6-Chloroquinazoline

Mol. form. $C_{14}H_{16}ClN_3O_2$

Yield quantitative

M.p. 215° to 216° C.

NMR delta (CDCl$_3$); 1.37(2H, m) 1.57(2H, quintet, J=7.4 Hz) 1.65(2H, quintet, J=7.4 Hz) 2.22(2H, t, J=7.2 Hz) 3.52(2H, dt, J=7.2, 5.2 Hz) 7.68(1H, d, J=8.8 Hz) 7.75(1H, dd, J=8.8, 2.4 Hz) 8.32(1H, brt, J=5.2 Hz) 8.40(1H, d, J=2.4 Hz) 8.46(1H, s) 11.98(1H, br-s)

EXAMPLE 11

4-(Carboxymethyl)Amino-6,7,8-Trimethoxyquinazoline

Mol. form. $C_{13}H_{15}N_3O_5$

Yield 54%

M.p. 121° to 123° C.

NMR delta (DMSO-d$_6$); 3.89(3H, s) 3.92(3H, s) 3.99(3H, s) 4.18(2H, d, J=5.6 Hz) 7.49(1H, s) 8.37(1H, s) 8.47(1H, brt, J=5.6 Hz)

EXAMPLE 12

4-(6-Carboxyhexyl)Amino-6,7,8-Trimethoxyquinazoline

Mol. form. $C_{18}H_{25}N_3O_5$

Yield 894%

M.p. 184° to 185° C.

NMR delta (DMSO-d$_6$); 1.28–1.42 (4H, m) 1.52(2H, m) 1.64(2H, m) 2.20(2H, t, J=7.2 Hz) 3.51(2H, m) 3.87(3H, s) 3.91(3H, s) 3.97(3H, s) 7.43(1H, s) 7.99(1H, brt, J=5.6 Hz) 8.35(1H, s)

EXAMPLE 13

4-(2-Carboxyethyl)Amino-6,7,8-Trimethoxyquinazoline

Mol. form. $C_{14}H_{17}N_3O_5$

Yield 56%

M.p. 236° to 237° C. (dec.)

NMR delta (DMSO-d$_6$); 2.65(2H, t, J=7.0 Hz) 3.37(2H, dt, J=7.0, 5.6 Hz) 3.88(3H, s) 3.91(3H, s) 3.98(3H, s) 7.43(1H, s) 8.1 1(1H, brt, J=5.6 Hz) 8.38(1H, s)

EXAMPLE 14

4-(4-Carboxybutyl)Amino-6,7,8-Trimethoxyquinazoline

Mol. form. $C_{16}H_{21}N_3O_5$

Yield 34%

M.p. 208° to 209° C. (dec.)

NMR 67 (DMSO-d$_6$); 1.54–1.72(4H, m) 2.28(2H, t, J=7.0 Hz) 3.54(2H, m) 3.87(3H, s) 3.91(3H, s) 3.97(3H, s) 7.44 (1H, s) 8.04(1H, brt, J=5.6 Hz) 8.35(1H, s) 12.01(1H, brs)

EXAMPLE 15

4-(7-Carboxyheptyl)Amino-6,7,8,-Trimethoxyquinazoline

Mol. form. $C_{19}H_{27}N_3O_5$

Yield 74%

M.p. 180° to 181° (dec.)

NMR delta (DMSO-d$_6$); 1.24–1.41(6H, m) 1.51(2H, m) 1.64(2H, m) 2.19(2H, t, J=7.4 Hz) 3.52(2H, m) 3.87(3H, s) 3.91(3H, s) 3.97(3H, s) 7.44(1H, s) 7.99(1H, brt, J=5.6 Hz) 8.35(1H, s) 11.94(1H, brs)

EXAMPLE 16

4-(5-Carboxypentyl)Amino-6,7,8-Trimethoxyquinazoline

Mol. form. $C_{17}H_{23}N_3O_5$

Yield 76%

M.p. 213° to 214° C. (dec.)

NMR delta (DMSO-d$_6$); 1.38(2H, m) 1.57(2H, m) 1.65 (2H, m) 2.23(2H, t J=7.2 Hz) 3.52(2H, dt, J=7.2, 5.6 Hz) 3.88(3H, s) 3.91(3H, s) 3.97(3H, s) 7.44(1H, s) 8.04(1H, brt, J=5.6 Hz) 8.35(1H, s) 11.99 (1H, brs)

EXAMPLE 17

4-[N-(3-Ethoxycarbonylpropl)-N-Methylamino]-6,7,8-Trimethoxyquinazoline Hydrochloride Mol. form. $C_{18}H_{25}N_3O_5$ HCl Yield 67%

M.p. 94° to 96° C. (dec.)

NMR delta (DMSO-d$_6$); 1.15(3H, t, J=7.2 Hz) 2.01(2H, m) 2.41(2H, t, J=7.2 Hz) 3.64(3H, br-s) 3.95(2H) 3.96(3H, s) 3.97(3H, s) 3.99(3H, s) 4.03(2H, q, J=7.2 Hz) 7.45(1H, s) 8.57(1H, s)

EXAMPLE 18

4-[N-(3-Carboxypropyl)-N-Methylamino]-6,7,8-Trimethoxyquinazoline

Mol. form. $C_{16}H_{21}N_3O_5$

Yield 87%

NMR delta (DMSO-d$_6$); 1.97 (2H, quintet, J=7.2 Hz) 2.27 (2H, t, J=7.2 Hz) 3.22(3H, s) 3.61(2H, t, J=7.2 Hz) 3.89(3H, s) 3.90(3H, s) 3.96(3H, s) 7.10(1H, s) 8.41(1H, s)

EXAMPLE 19

4-(4-Ethoxycarbonylpiperidino)-6,7,8-Trimethoxyquinazoline

Mol. form. $C_{19}H_{25}N_3O_5$

Yield 88%

M.p. oily substance

NMR delta (DMSO-d$_6$); 1.30 (3H, t, J=7.0 Hz) 1.98(2H, m) 2.12(2H, m) 2.63(1H, m) 3.14(2H, m) 3.97(3H, s) 4.06(3H, 4.10(2H, m) 4.13(3H, s) 4.19(2H, q, J=7.0 Hz) 6.92(1H, s) 8.73(1H, s)

EXAMPLE 20

4-(4-Carboxypiperidino)-6,7,8-Trimethoxyquinazoline

Mol. form. $C_{17}H_{21}N_3O_5$
Yield 77%
M.p. 233° to 234° C. (dec.)
Mass 348(M<+>+1)
NMR delta (DMSO-$d_6$); 1.80(2H, m) 1.99(2H, m) 2.59 (1H, m) 3.18(2H, m) 3.92(3H, s) 3.93(3H, s) 4.01(3H, s) 4.09(2H, m) 6.69(1H, s) 8.55(1H, s) 12.29(1H, br-s)

EXAMPLE 21

4-(6-Ethoxycarbonylhexyl)Amino-6,7,8-Trimethoxyquinazoline

Mol. form. $C_{20}H_{29}N_3O_5$
Yield 98%
M.p. 132° to 133° C.
Mass 392° (M<+>+1)
NMR delta (CDCl$_3$); 1.25(3H, t, J=7.2 Hz) 1.36–1.51(4H, m) 1.60–1.79(4H, m) 2.31(2H, t, J=7.2 Hz) 3.65(2H, dt, J=7.2, 5.6 Hz) 3.98(3H, s) 4.03(3H, s) 4.12(3H, s) 4.13(2H, q, J=7.2 Hz) 5.54(1H, brs) 6.72(1H, s) 8.62(1H, s)

EXAMPLE 22

4-(5-Ethoxycarbonylpentyl)Amino-6-Chloroquinazoline

Mol. form. $C_{16}H_{20}ClN_3O_2$
Yield 84%
M.p. 117° to 118° C.
Mass 322 (M<+>+1)
NMR delta (CDCl$_3$); 1.27(3H, t, J=7.2 Hz) 1.49(2H, m) 1.68–1.80(4H, m) 2.37(2H, t, J=7.0 Hz) 3.71(2H, dt, J=6.8, 5.6 Hz) 4.18(2H, q, J=7.2 Hz) 6.03(1H, brs) 7.66(1H, dd, J=9.2, 2.4 Hz) 7.77(1H, d, J=9.2 Hz) 7.82(1H, d, J=2.4 Hz) 8.64(11, s)

EXAMPLE 23

4-[N-(3-Ethoxycarbonylpropyl-N-methylamino)-6,7,8-trimethoxyquinazoline hydrochloride Mol. form. $C_{18}H_{25}N_3O_5$ HCl
Yield 67%
M.p. 94° to 96° C.
NMR delta (DMSO-$d_6$); 1.15(3H, t, J=7.2 Hz) 2.01(2H, m) 2.41(2H, t, J=7.2 Hz) 3.64(3H, brs) 3.95(2H) 3.96(3H, s) 3.97(3H, s) 3.99(3H, s) 4.03(2H, q, J=7.2 Hz) 7.45(1H, s) 8.57(1H, s)

EXAMPLE 24

4-(3-Ethoxycarbonylpropyl)Amino-6,8-Dimethoxyquinzoline

Mol. form. $C_{16}H_{21}N_3O_4$
Yield 90%
M.p. 133° to 134° C.
Mass 320(M<+>+1)
NMR delta (CDCl$_3$); 1.25(3H, t, J=7.2 Hz) 2.10(2H, quintet, J=6.4 Hz) 2.55(2H, t, J=6.4 Hz) 3.69(2H, dt,=6.4, 4.8 Hz) 3.93(3H, s) 4.00(3H, s) 4.14(2H, q, J=7.2 Hz) 6.49(1H, brs) 6.61(1H, d, J=2.4 Hz) 6.75(1H, d, J=2.4 Hz) 8.59(1H, s)

EXAMPLE 25

4-(3-Ethoxycarbonylproypl)Amino-8-Methoxyquinazoline

Mol. form. $C_{15}H_{29}N_3O_3$
Yield 64%
M.p. 128° to 129° C.
Mass 290(M<+>+1)
NMR delta (CDCl$_3$); 1.24 (3H, t, J=7.2 Hz) 2.09 (2H, quintet, J=6.4 Hz) 2.53(2H, t, J=6.4 Hz) 4.04(3H, s) 4.15 (2H, q, J=7.2 Hz) 6.44(1H, brs) 7.11 (1H, dd, J=8.0, 0.8 Hz) 7.30(1H, dd, J=8.0, 0.8 Hz) 7.4(1H, t, J=8.0 Hz) 8.69(1H, s)

EXAMPLE 26

4-(3-Ethoxycarbonylpropylamino-6-Chloroquinazoline

Mol. form. $C_{14}H_{16}ClN_3O_2$
Yield 57%
M.p. 91° to 92° C.
Mass 294(M<+>+1)
NMR delta (CDCl$_3$); 1.26(3H, t, J=7.2 Hz) 2.10(2H, quintet, J=6.4 Hz) 2.54(2H, t, J=6.4 Hz) 3.70(2H, dt, J=6.4, 5.2 Hz) 4.18(2H, q, J=7.2 Hz) 6.60(1H, brs) 7.66(1H, dd, J=9.2,2.0 Hz) 7.76(1H, d, J=2.0 Hz) 7.77(1H, d,, J=9.2 Hz) 8.63(1H, s)

EXAMPLE 27

4-(3-Ethoxycarbonylpropyl)Amino-7-Chloroquinazoline

Mol. form. $C_{14}H_{16}ClN_3O_2$
Yield 36%
M.P. 90° to 91° C.
Mass 294(M<+>+1)
NMR delta (CDCl$_3$); 1.25(3H, t, J=7.2 Hz) 2.09(2H, quintet, J=6.4 Hz) 2.55(2H, t, J=6.4 Hz) 3.70(2H, dt, J=6.4, 4.8 Hz) 4.16(2H, q, J=7.2 Hz) 6.74(1H, brs) 7.42(1H, dd, J=8.8, 2.0 Hz) 7.71 (1H, d, J=8.8 Hz) 7.81 (H, d, J=2.0 Hz) 8.62(1H, s)

EXAMPLE 28

4-(Carboxymethyl)Amino-6,7,8-Trimethoxyquinazoline

Mol. form. $C_{13}H_{15}N_3O_5$
Yield 54%
M.p. 121° to 123° C.
Mass 294(M<+>+1)
NMR delta (DMSO-$d_6$); 3.89(3H, s) 3.92(3H, s) 3.99(3H, s) 4.18(2H, d, J=5.6 Hz) 7.49(1H, s) 8.37(1H, s) 8.47(1H, brt, J=5.6 Hz)

EXAMPLE 29

4-(6-Carboxyhexyl)Amino-6,7,8-Trimethoxyquinazoline

Mol. form. $C_{18}H_{25}N_3O_5$
Yield 89%
M.p. 184° to 185° C.
Mass 364 (M<+>+1)
NMR delta (DMSO$_6$); 1.28–1.42(4H, m) 1.52(2H, m) 1.64(2H, m) 2.20(2H, t, J=7.2 Hz) 3.51(2H, m) 3.87(3H, s) 3.91(3H, s) 3.97(3H, s) 7.43(1H, s) 7.99(1H, brt, J=5.6 Hz) 8.35(1H, s)

EXAMPLE 30

4-[N-(3-Carboxypropyl)-N-Methylamino]-6,7,8-Trimethoxyquinazoline

Mol. form. $C_{16}H_{21}N_3O_5$
Yield 87%
M.p. 133° to 135° C.
NMR delta (DMSO$_6$); 1.97(2H, quintet, J=7.2 Hz) 2.27 (2H, t, J=7.2 Hz) 3.22 (3H, s) 3.61(2H, t, J=7.2 Hz) 3.89(3H, s) 3.90(3H, s) 3.96(3H, s) 7.10(1H, s) 8.41(1H, s)

EXAMPLE 31

4-(3-Carboxypropyl)Amino-6,8-Dimethoxyquinazoline

Mol. form. $C_{14}H_{17}N_3O_4$
Yield 51%
M.p. 217° to 218° C. (dec.)
NMR 5 (DMSO$_6$); 1.89(2H, quintet, J=7.2 Hz) 2.33 (2H, t, J=7.2 Hz) 3.55(2H, dt, J=7.2, 5.6 Hz) 3.88(3H, s) 3.89(3H, s) 6.83(1H, d, J=2.4 Hz) 7.17(1H, d, J=2.4 Hz) 7.99(1H, brt, J=5.6 Hz) 8.31(1H, s)

EXAMPLE 32

4-(4-Cyanobutyl)Amino-6,7,8-Trimethoxyquinazoline

Mol. form. $C_{16}H_{20}N_4O_5$
Yield 94%
M.p. 160° to 161° C.
Mass 317 (M<+>+1)
NMR delta (DMSO-d$_6$); 1.81(2H, m) 1.94(2H, m) 2.47 (2H, t, J=6.8 Hz) 3.75(2H, dt, J=6.8, 6.0 Hz) 4.00(3H, s) 4.03(3H, s) 4.11(3H, s) 5.91(1H, brs) 6.82(1H, s) 8.60(1H, s)

EXAMPLE 33

4-(5-Cyanopentyl)Amino-6,7,8-Trimethoxyquinazoline

Mol. form. $C_{17}H_{22}N_4O_5$
Yield 75%
M.p. 155° to 156° C.
Mass 331 (M<+>+1)
NMR delta (DMSO-D6); 1.60–1.80(6H, m) 2.40(2H, t, J=7.0 Hz) 3.70(2H, dt, J=7.0, 5.6 Hz) 4.00 (3H, s) 4.03(3H, s) 4.11(3H, s) 6.00 (1H, brs) 6.84(1H, s) 8.60(1H, s)

EXAMPLE 34

4-(2-Hydroxyethyl)Amino-6,7,8-Trimethoxyquinazoline

Mol. form. $C_{13}H_{17}N_3O_4$
Yield 80%
M.p. 183° to 185° C.
Mass 280 (M<+>+1)
NMR delta (CDCl$_3$); 3.78(2H, m) 3.88(2H, m) 3.99(3H, s) 4.03(3H, s) 4.10(3H, s) 7.10(1H, brs) 7.13(1H, s) 8.53(1H, s)

EXAMPLE 35

4-(3-Hydroxypropyl)Amino-6,7,8-Trimethoxyquinazoline

Mol. form. $C_{14}H_{19}N_3O_4$
Yield 76%
M.p. 179° to 180° C.
Mass 294 (M<+>+1)
NMR delta (CDCl$_3$); 1.89(2H, m) 3.70(2H, t, J=5.4 Hz) 3.85(2H, q, J=6.0 Hz) 3.97(3H, s) 4.03(3H, s) 4.11(3H, s) 6.07(1H, brs) 6.72(1H, s) 8.56(1H, s)

EXAMPLE 36

4-(4-Hydroxybutyl)Amino-6,7,8-Trimethoxyquinazoline

Mol. form. $C_{15}H_{21}N_3O_4$
Yield 74%
M.p. 171° to 182° C.
Mass 308 (M<+>+1)
NMR delta (CDCl$_3$); 1.74(2H, m) 1.88(2H, quintet, J=6.8 Hz) 3.69(2H, dt, J=6.8, 5.6 Hz) 3.80 (2H, t, J=6.0 Hz) 3.96 (3H, s) 4.03(3H, s) 4.11(3H, s) 6.17(1H, brs) 6.77(1H, s) 8.59(1H, s)

EXAMPLE 37

[3-(Imidazol-1-Yl)Propyl]Amino-6,7,8-Trimethoxyquinazoline

Mol. form. $C_{17}H_{21}N_5O_3$
Yield 82%
M.p. 192° to 194° C.
Mass 344 (M<+>+1)
NMR delta (DMSO-d6); 2.13(2H, quintet, J=7.0 Hz) 3.53(2H, m) 3.88(3H, s) 3.92(3H, s) 3.97(3H, s) 4.13(2H, t, J=7.0 Hz) 7.07(1H, s) 7.35(1H, s) 7.47(1H, s) 8.00(1H, s) 8.20(1H, t, J=5.4 Hz) 8.38(1H, s)

EXAMPLE 38

6-Chloro-4-[3-(Imidazol-1-yl)Propyl]Aminoquinazoline

Mol. form. $C_{17}H_{14}ClN_5$
Yield 63%
M.p. 165° to 168° C.
Mass 288(M<+>+1)
NMR delta (CDCl$_3$); 2.24(2H, quintet, J=6.4 Hz) 3.64 (2H, q, J=6.4 Hz) J 6.4 Hz) 7.08(1H, s) 7.09(1H, s) 4.14(2H, t, 7.64(1H, dd, J=8.8, 2.4 Hz) 7.73(1H, d, J=8.8 Hz) 7.92 (1H, s) 8.06(1H, brs) 8.38(1H, d, J=2.4 Hz) 8.58(1H, s)

EXAMPLE 39

4-Dipropylamino-6,7,8-trimethoxyquinazoline Hydrochloride

Mol. form. $C_{17}H_{25}N_3O_3$ HCl
Yield 78%
M.p. 169° to 170° C.
NMR delta (CDCl$_3$); 1.08(6H, t, J=7.2 Hz) 1.92(4H, brm) 3.80(4H, m) 3.97(3H, s) 4.09(3H, s) 4.19(3H, s) 7.02(1H, s) 8.78(1H, s)

EXAMPLE 40

4-Propylamino-6,7-trimethoxyquinazoline

Mol. form. $C_{14}H_{19}N_3O_3$
Yield 87%
NMR delta (CDCl$_3$); 1.05(3H, t, J=7.2 Hz) 1.77 (2H, sextet, J=7.2 Hz) 3.62(2H, dt, J=7.2, 6.0 Hz) 3.98(3H, s) 4.03(3H, s) 4.12(3H, s) 5.50(1H, brs) 6.69(1H, s) 8.63(1H, s)

EXAMPLE 41

4-Diethylamino-6,7,8-trimethoxyquinazoline Hydrochloride

Mol. form. $C_{15}H_{21}N_3O_3$ HCl
Yield quantitative
M.p. 122° to 123° C.
Mass 292 (M<+>+1)
NMR delta (CDCl$_3$); 1.51(6H, t, J=6.8 Hz) 3.93(4H, q, J=6.8 Hz) 3.98(3H, s) 4.10(3H, s) 4.20(3H, s) 7.08(1H, s) 8.80(1H, s)

EXAMPLE 42

4-Diethylamino-6,7-dimethoxyquinazaline Hydrochloride

Mol. form. $C_{14}H_{19}N_3O_2$ HCl
Yield 87%
M.p. 218° to 219° C.
NMR delta (CDCl$_3$); 1.51(6H, t, J=7.2 Hz) 3.91(4H, q, J=7.2 Hz) 3.99(3H, s) 4.10(3H, s) 7.25(1H, s) 7.93(1H, s) 8.47(1H, d, J=2.8 Hz)

EXAMPLE 43

4-Diethylamino-6,8-Dimethoxyquinazoline Hydrochloride

Mol. form. $C_{14}H_{19}N_3O_2$ HCl
Yield quantitative
M.p. 160° to 161° C.
NMR delta (CDCl$_3$); 1.51(6H, brt) 3.91(3H, s) 3.94(4H, q, J=7.2 Hz) 4.10 (3H, s) 6.85(1H, d, J=2.4 Hz) 6.91(1H, d, J=2.4 Hz) 8.82(1H, s)

EXAMPLE 44

4-Diethylaminoquinazoline Hydrochloride

Mol. form. $C_{12}H_{15}N_3$ HCl
Yield 96%
M.p. 207° to 208° C.
NMR delta (CDCl$_3$); 1.52(6H, brs) 3.97(4H, q, J=7.2 Hz) 7.64(1H, ddd, J=8.6, 7.2, 1.0 Hz) 7.90(1H, ddd, J=8.4, 7.2, 1.0 Hz) 7.98(1H, dd, J=8.6, 1.0 Hz) 8.49(1H, dd, J=8.4.1.0 Hz) 8.59(1H, s)

EXAMPLE 45

4-Diethylamino-8-Methoxyquinazoline Hydrochloride

Mol. form. $C_{13}H_{17}N_3O$ HCl
Yield 96%
M.p. 198° to 199° C.
NMR delta (CDCl$_3$); 1.51(6H, brs) 3.96(4H, q, J=7.2 Hz) 4.13(3H, s) 7.29(1H, dd, J=7.6, 1.4 Hz) 7.51(1H, dd, J=8.8, 1.4 Hz) 7.55(1H, dd, J=8.8, 7.6 Hz) 8.93(1H, s)

EXAMPLE 46

7-Chloro-4-Diethylaminoquinazoline Hydrochloride

Mol. form. $C_{12}H_{14}ClN_3$ HCl
Yield 61%
M.p. 245° to 247° C.
NMR delta (CDCl$_3$); 1.53(6H, brs) 3.95(4H, q, J=7.2 Hz) 7.57(1H, dd, J=9.2, 2.0 Hz) 7.89(1H, d, J=9.2 Hz) 8.51(1H, d, J=2.0 Hz) 8.57(1H, s)

EXAMPLE 47

6-Chloro-4-Diethylaminoquinazoline Hydrochloride

Mol. form. $C_{12}H_{14}ClN_3$ HCl
Yield 66%
M.p. 219° to 220° C.
NMR delta (CDCl$_3$); 1.64(6H, brs) 3.96(4H, q, J=7.2 Hz) 7.85(1H, dd, J 8.8, 2.0 Hz) 7.93(1H, d, J=2.0 Hz) 8.54(1H, d, J=8.8 Hz) 8.58(1H, s)

EXAMPLE 48

6-Chloro-4-Cyclopentylaminoquinazoline Hydrochloride

Mol. form. $C_{13}H_{14}ClN_3$ HCl
Yield 87%
M.p. 239° to 241° C.
NMR delta (CDCl$_3$); 1.65–1.74(2H, m) 1.88–2.00(2H, m) 2.00–2.12(2H, m) 2.12–2.22(2H, m) 4.86(1H, sextet, J=7.4 Hz) 7.61(1H, dd, J=8.8, 2.0 Hz) 8.12(1H, d, J=8.8 Hz) 8.55(1H, s) 9.20(1H, d, J=2.0 Hz) 9.86(1H, brd, J=7.4 Hz)

EXAMPLE 49

4-Diethylamino-5,6-Dimethoxiquinazoline

Mol. form. $C_{14}H_{19}N_3O_2$
Yield 70%
M.p. oily substance
NMR delta (CDCl$_3$); 1.23(6H, t, J=7.0 Hz) 3.61(4H, q, J=7.0 Hz) 3.72(3H, s) 3.98(3H, s) 7.49(1H, d, J=9.0 Hz) 7.63(1H, d, J=9.01 Hz) 8.47(1H, s)

EXAMPLE 50

4-Diethylamino-2-Methyl-6,7,8-Trimethoxyquinazoline Hydrochloride

Mol. form. $C_{16}H_{23}N_3O_3$ HCl
Yield 85%
M.p. 186° to 187° C.
NMR delta (CDCl$_3$); 1.49(6H, q, J=7.0 Hz) 3.05(3H, s) 3.90(4H, J=7.0 Hz) 3.96(3H, s) 4.08(3H, s) 6.98(1H, s).

EXAMPLE 51

2-Chloro-4-Diethylamino-6,7,8-Trimethoxyquinazoline

Mol. form. $C_{15}H_{20}ClN_3O_3$
Yield 75%
M.p. 107° to 108° C.
NMR delta (CDCl$_3$); 1.40(6H, q, J=7.2 Hz) 3.70(4H, q, J=7.2 Hz) 3.93(3H, s) 4.05(3H, s) 4.08(3H, s) 6.98(1H, s)

EXAMPLE 52

4-Diethylamino-2-(4-Hydroxypiperidino)-6,7,8-Trimethoxyquinazoline

Mol. form. $C_{20}H_{30}N_4O_4$ HCl
Yield 53%

M.p. 77° to 78° C.

NMR delta (CD3OD); 1.48(6H, t, J=7.2 Hz) 1.63(2H, m) 2.00(2H, m) 3.59(2H, m) 3.89(4H, q, J=7.2 Hz) 3.95(3H, s) 3.97(1H, m) 4.02(3H, s) 4.06(3H, s) 4.16(2H, m) 7.15(1H, s)

EXAMPLE 53

4-Diethylamino-2-(4-Ethoxycarbonylpiperidino)-6,7,8-Trimethoxyquinazoline

Mol. form. $C_{23}H_{34}N_4O_5$
Yield 36%
M.p. 80° to 81° C.

NMR delta (CDCl$_3$); 1.26(3H, t, J=7.2 Hz) 1.34(6H, t, J=7.2 Hz) 1.73(2H, m) 1.97(2H, m) 2.55(1H, m) 3.02(2H, m) 3.58(4H, q, J=7.2 Hz) 3.88(3H, s) 4.03(3H, s) 4.08(3H, s) 4.14(2H, q, J=7.2 Hz) 4.78(2H, m) 6.88(1H, s)

EXAMPLE 54

2-(4-Carboxypiperidino)-4-Diethylamino-6,7,8-Trimethoxyquinazoline

Mol. form. $C_{17}H_{30}N_4O_5$
Yield 38%

NMR delta (DMSO-d6); 1.31(6H, t, J=7.0 Hz) 1.50(2H, m) 1.87(2H, m) 2.52(1H, m) 3.02(2H, m) 3.58(4H, brs) 3.83(3H, s) 3.85(3H, s) 3.95(3H, s) 4.57(2H, m) 6.89(1H, s) 12.23(1H, brs)

EXAMPLE 55

6-Bromo-4-Diethylamino-7,8-Dimethoxyquinazoline Hydrochloride

Mol. form. $C_{14}H_{18}BrN_3O_2$ HCl
Yield 75%

NMR delta (CDCl3) 1.50(6H, brs) 3.93(4H, q, J=7.0 Hz) 4.13(3H, s) 4.19(3H, s) 7.94(1H, s) 8.84(1H, s)

EXAMPLE 56

4-(4-Carbamoylpiperidino)-6,7,8-Trimethoxyquinazoline

Mol. form. $C_{17}H_{22}N_4O_4$
Yield 81%
M.p. 165° to 166° C.
Mass 347 (M<30>+1)

NMR delta (CDCl$_3$) 2.00–2.10(4H, m) 2.50(1H, m) 3.09(2H, m) 3.97(3H, s) 4.06(3H, s) 4.13(3H, s) 4.20(2H, m) 5.56(1H, brs) 5.64(1H, brs) 6.93(1H, s) 8.73(1H, s)

EXAMPLE 57

4-[4-(4-Fluorobenzoyl)Piperidino]-6,7,8-Trimethoxyquinazoline

Mol. form. $C_{23}H_{24}FN_3O_4$
Yield 84%
M.p. 137° to 138° C.
Mass 426 (M<+>+1)

NMR delta (CDCl$_3$) 2.03–2.15(4H, m) 3.21(2H, m) 3.56(1H, m) 3.97(3H, s) 4.07(3H, s) 4.14(3H, s) 4.23(2H, m) 6.95(1H, s) 7.19(2H, m) 8.04(2H, m) 8.75(1H, s)

EXAMPLE 58

4-[4-(4-Fluoro-α-Hydroxybenzyl)Piperidino]-6,7,8-Trimethoxyquinazoline

Mol. form. $C_{23}H_{26}FN_3O_4$
Yield 90%

M.p. 187° to 188° C.
Mass 428 (M<+>+1)

NMR delta (CDCl$_3$) 1.42–1.53(2H, m) 1.57–1.68(2H, m) 1.92(1H, m) 2.16(1H, m) 2.92–3.07(2H, m) 3.95(3H, s) 4.05(3H, s) 4.12(3H, s) 4.10–4.30(2H, m) 4.49(1H, d, J=7.2 Hz) 6.90(1H, s) 7.07(2H, m) 7.33(2H, m) 8.70(1H, s)

EXAMPLE 59

4-(4-Dimethylaminopiperidino)-6,7,8-Trimethoxyquinazoline Dihydrochloride

Mol. form. $C_{18}H_{26}N_4O_3$ 2HCl
Yield 55%
M.p. 197° to 198° C. (dec.)
Mass 347 (<+>+1)

NMR delta (CDCl$_3$) 1.90(2H, m) 2.29(2H, m) 2.73(6H, d, J=5.2 Hz) 3.55(2H, m) 3.66(1H, m) 4.010(3H, s) 4.012(3H, s) 4.03(3H, s) 4.84(2H, m) 7.24(1H, s) 8.70(1H, s) 11.35(1H, brs)

EXAMPLE 60

4-(4-Piperidinopiperidino)-6,7,8-Trimethoxyquinazoline Dihydrochloride

Mol. form. $C_{21}H_{30}N_{4O3}$ 2HCl
Yield 92%
M.p. 219° to 220° C. (dec.)
Mass 347 (M<+>+1)

NMR delta (CDCl$_3$) 1.55(1H, m) 1.82–2.08(7H, m) 2.40(2H, m) 3.05(2H, m) 3.53–3.75(5H, m) 4.06(3H, s) 4.10(3H, s) 4.13(3H, s) 5.05(2H, m) 7.24(1H, s) 8.58(1H, s)

EXAMPLE 61

4-(4-Oxopiperidino)-6,7,8-trimethoxyquinazoline

Mol. form. $C_{16}H_{19}N_3O_4$
Yield 66%
M.p. 135° to 136° C.
Mass 318 (M<+>+1)

NMR delta (CDCl$_3$) 2.68(4H, t, J=6.0 Hz) 3.98(3H, s) 4.00(4H, J=6.0 Hz) 4.08(3H, s) 4.15(3H, s) 6.97(1H, 8.77(1H, s)

EXAMPLE 62

4-(4-Hydroxypiperidino)-6,7,8-Trimethoxyquinazoline

Mol. form. $C_{16}H_{21}N_3O_4$
Yield 83%
M.p. 150° to 151° C.
Mass 320 (M<+>+1)

NMR delta (CDCl$_3$) 1.79(2H, m) 2.11(2H, m) 3.33(2H, m) 3.97(3H, s) 3.98–4.08(3H, m) 4.06(3H, s) 4.13(3H, s) 6.92(1H, s) 8.72(1H, s)

EXAMPLE 63

4-Pyrrolidino-6,7,8-Trimethoxyquinazoline Hydrochloride

Mol. form. $C_{15}H_{19}N_3O_3$ HCl
Yield 11%
M.p. 156° to 157° C.

Mass 290 (M<+>+1)

NMR delta (CDCl₃) 2.12(2H, brs) 2.23(2H, brs) 4.00(2H, brs) 4.03(3H, s) 4.09(3H, s) 4.16(3H, s) 4.29(2H, brs) 7.39(1H, s) 8.64(1H, s)

EXAMPLE 64

4-Piperidino-6,7,8-Trimethoxyquinazoline Hydrochloride

Mol. form. $C_{16}H_{21}N_3O_3$ HCl

Yield 85%

M.p. 145° to 146° C.

Mass 304 (M<+>+1)

NMR delta (CDCl₃) 1.87(6H, brs) 3.98(3H, s) 4.09(3H, s) 4.11(4H, brt) 4.19(3H, s) 6.95(1H, s) 8.75(1H, s)

EXAMPLE 65

4-[4-(2-Pyrimidyl)Piperazin-1-Yl]-6,7,8-Trimethoxyquinazoline

Mol. form. $C_{19}H_{22}N_6O_3$

Yield 86%

M.p. 157° to 158° C.

Mass 383 (M<+>+1)

NMR delta (CDCl₃) 3.75(4H, m) 3.97(3H, s) 4.06(4H, m) 4.08(3H, s) 4.14(3H, s) 6.57(1H, t, J=4.8 Hz) 6.99(1H, s) 8.37(2H, d, J 4.8 Hz) 8.76(1H, s)

EXAMPLE 66

4-[4-(2-Pyridyl)Piperazin-1-yl]-6,7,8-Trimethoxyquinazoline

Mol. form. $C_{20}H_{23}N_5O_3$

Yield 80%

M.p. 145° to 146° C.

Mass 382 (M<+>+1)

NMR delta (CDCl₃) 3.79(8H, brs) 3.97(3H, s) 4.08(3H, s) 4.14(3H, s) 6.69 (1H, ddd, J=7.2, 4.8, 0.8 Hz) 6.75(1H, dt, J=8.8, 0.8 Hz) 7.00(1H, s) 7.55(1H, ddd, J=8.8, 7.2, 2.0 Hz) 8.24(1H, ddd, J=4.8, 2.0, 0.8 Hz) 8.77(1H, s)

EXAMPLE 67

4-(4-Dimethylaminopiperidino)-6,7,8-Trimethoxyquinazoline

Mol. form. $C_{18}H_{26}N_4O_3$

Yield 42%

M.p. 182° to 184° C.

Mass 347 (M<+>+1)

NMR delta (CDCl₃) 2.05(2H, m) 2.36(2H, m) 2.82(6H, s) 3.15(2H, m) 3.37(1H, m) 3.98(3H, s) 4.07(3H, s) 4.14(3H, s) 4.36(2H, m) 6.87(1H, s) 8.75(1H, s)

EXAMPLE 68

4-Morpholino-6,7,8-Trimethoxyquinazoline Hydrochloride

Mol. form. $C_{15}H_{19}N_3O_4$ HCl

Yield 84%

M.p. 158° to 159° C.

Mass 306 (M<+>+1)

NMR delta (CDCl₃) 3.87(4H, t, J=4.4 Hz) 3.99(3H, s) 4.11(3H, s) 4.20(3H, s) 4.24(4H, t, J=4.4 Hz) 6.93(1H, s) 8.82(1H, s)

EXAMPLE 69

4-(3-Carboxypropyl)amino-6-Chloroquinazoline

Mol. form. $C_{12}H_{12}ClN_3O_2$

Yield 78%

M.p. 257° to 258° C. (dec.)

NMR delta (DMSO-d6); 1.85(2H, quintet, J=7.2 Hz) 2.31(2H, t, J=7.2 Hz) 3.52(2H, dt, J=7.2, 5.2 Hz) 7.67(1H, d, J=8.8 Hz) 7.75(1H, dd, J=8.8, 2.4 Hz) 8.34(1H, brt, J=5.2 Hz) 8.39(1H, d, J=2.4 Hz) 8.44(1H, s) 12.07(1H, brs)

EXAMPLE 70

4-(3-Carboxypropyl)amino-7-Chloroquinazoline

Mol. form. $C_{12}H_{12}N_3O_2$

Yield 89%

M.p. 243° to 244° C. (dec.)

NMR delta (DMSO-d6); 1.87(2H, quintet, J=7.2 Hz) 2.33(2H, t, J=7.2 Hz) 3.55(2H, dt, J=7.2, 5.6 Hz) 7.67(1H, dd, J=8.8, 2.4 Hz) 7.71(1H, d, J=2.4 Hz) 8.28(1H, d, J=8.8 Hz) 8.44(1H, brt, J=5.6 Hz) 8.46(1H, s) 12.09(1H, brs)

EXAMPLE 71

6-Chloro-4-Diethylamino-7,8-Dimethoxyquinazoline Hydrochloride

Mol. form. $C_{14}H_{18}ClN_3O_2$ HCl

Yield 83%

M.p. 129° to 130° C. (dec.)

NMR delta (CDCl₃); 1.87(2H, quintet, J=7.2 Hz) 2.33 (2H, t, J=7.2 Hz) 3.55(2H, dt, J=7.2, 5.6 Hz) 7.67(1H, dd, J=8.8, 2.4 Hz) 7.71(1H, d, J=2.4 Hz) 8.28(1H, d, J=8.8 Hz) 8.44(1H, brt, J=5.6 Hz) 8.46(1H, s) 12.09(1H, brs)

EXAMPLE 72

6-Bromo-4-Diethylamino-7,8-Dimethoxyquinazoline Hydrochloride

Mol. form. $C_{14}H_{18}N_3O_2$ HCl

Yield 75%

M.p. 148° to 149° C.

NMR delta (CDCl₃); 1.50(6H, brs) 3.93(4H, q, J=7.0 Hz) 4.13(3H, s) 4.19(3H, s) 7.94(1H, s) 8.84(1H, s)

EXAMPLE 73

4-Diethylamino-7-Methoxy-6-Methylthioquinazoline Hydrochloride

Mol. form. $C_{14}H_{19}N_3O_2$ HCl

Yield 67%

M.p. 213° to 214° C.

NMR delta (CDCl₃); 1.51(6H, t, J=7.0 Hz) 2.51(3H, s) 3.92(4H, q, J=7.0 Hz) 4.11(3H, s) 7.55(1H, s) 7.86(1H, s) 8.48(1H, s)

It will be understood that various changes and modifications can be made in the details of procedure, formulation and use without departing from the spirit of the invention, especially as defined in the following claims.

We claim:

1. A method for inhibiting the growth of neoplastic cells in a mammal comprising administering to said mammal with neoplastic cells sensitive to such a compound a growth inhibiting effective amount of a compound of Formula I:

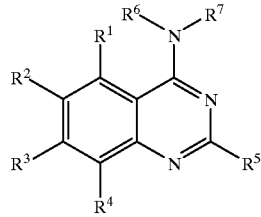

wherein $R_1$, $R_2$, $R_3$, $R_4$ and $R_5$ are independently selected from the group consisting of hydrogen, halogen, lower alkyl, or lower alkoxy; and $R_6$ and $R_7$ are independently selected from the group consisting of hydrogen, lower alkyl, hydroxy(lower) alkyl lower alkoxyalkyl, cyano(lower)alkyl, lower cycloalkyl, cycloalkylalkyl or carboxyl lower alkyl.

2. The method of claim 1 wherein $R_1$–$R_5$ are independently selected from the group consisting of hydrogen, halogen, lower alkyl or lower alkoxy; and $R_6$ and $R_7$ are independently selected from the group consisting of hydrogen, lower alkyl or a carboxyl lower alkyl.

3. The method of claim 2 wherein $R_1$ and $R_5$ are hydrogen, and $R_2$, $R_3$ and $R_4$ are independently selected from the group consisting of halogen or lower alkoxy.

4. The method of claim 3 wherein $R_1$ and $R_5$ are hydrogen, and $R_2$, $R_3$ and $R_4$ are lower alkoxy, and wherein $R_6$ and $R_7$ are independently selected from the group consisting of hydrogen, n-propyl or carboxypropyl.

5. The method of claim 1 wherein the compound is selected from the group consisting of: 4-(3-ethoxycarbonylpropyl)amino-6,7,8-trimethoxy-quinazoline; 4-(3-carboxypropyl)amino-6,7,8-trimethoxy-quinazoline; 4-(5-ethoxycarbonylpentyl)amino-6,7,8-trimethoxy-quinazoline; 4-(5-ethoxycarbonylpentyl)amino-6-chloro-quinazoline; 4-(ethoxycarbonylmethyl)amino-6,7,8-trimethoxy-quinazoline; 4-(6-ethoxycarbonylhexyl)amino-6,7,8-trimethoxy-quinazoline; 4-(2-ethoxycarbonylethyl)amino-6,7,8-trimethoxy-quinazoline; 4-(4-ethoxycarbonylbutyl)amino-6,7,8-trimethoxy-quinazoline; 4-(7-ethoxycarbonylheptyl)amino-6,7,8-trimethoxy-quinazoline; 4-(5-carboxypentyl)amino-6-chloroquinazoline; and 4-(carboxymethyl)amino-6,7,8-trimethoxy-quinazoline.

6. A method of treating a mammal having precancerous lesions comprising administering to said mammal having lesions sensitive to such compound a pharmacologically effective amount of a compound of Formula I:

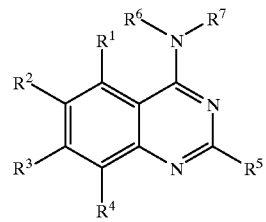

wherein $R_1$, $R_2$, $R_3$, $R_4$ and $R_5$ are independently selected from the group consisting of hydrogen, halogen, lower alkyl, or lower alkoxy; and $R_6$ and $R_7$ are independently selected from the group consisting of hydrogen, lower alkyl, hydroxy(lower) alkyl, lower alkoxyalkyl, cyano(lower)alkyl, lower cycloalkyl, cycloalkylalkyl or carboxyl lower alkyl.

7. The method of claim 6 wherein $R_1$–$R_5$ are independently selected from the group consisting of hydrogen, halogen, lower alkyl or lower alkoxy; and $R_6$ and $R_7$ are independently selected from the group consisting of hydrogen, lower alkyl or a carboxyl lower alkyl.

8. The method of claim 7 wherein $R_1$ and $R_5$ are hydrogen, and $R_2$, $R_3$ and $R_4$ are independently selected from the group consisting of halogen or lower alkoxy.

9. The method of claim 8 wherein $R_1$ and $R_5$ are hydrogen, and $R_2$, $R_3$ and $R_4$ are lower alkoxy, and wherein $R_6$ and $R_7$ are independently selected from the group consisting of hydrogen, n-propyl or carboxypropyl.

10. The method of claim 6 wherein the compound is selected from the group consisting of: 4-(3-ethoxycarbonylpropyl)amino-6,7,8-trimethoxy-quinazoline; 4-(3-carboxypropyl)amino-6,7,8-trimethoxy-quinazoline; 4-(5-ethoxycarbonylpentyl)amino-6,7,8-trimethoxy-quinazoline; 4-(5-ethoxycarbonylpentyl)amino-6-chloro-quinazoline; 4-(ethoxycarbonylmethyl)amino-6,7,8-trimethoxy-quinazoline; 4-(6-ethoxycarbonylhexyl)amino-6,7,8-trimethoxy-quinazoline; 4-(2-ethoxycarbonylethyl)amino-6,7,8-trimethoxy-quinazoline; 4-(4-ethoxycarbonylbutyl)amino-6,7,8-trimethoxy-quinazoline; 4-(7-ethoxycarbonylheptyl)amino-6,7,8-trimethoxy-quinazoline; 4-(5-carboxypentyl)amino-6-chloroquinazoline; and 4-(carboxymethyl)amino-6,7,8-trimethoxy-quinazoline.

* * * * *